United States Patent [19]

Sundheimer et al.

[11] 4,354,514
[45] Oct. 19, 1982

[54] APPARATUS FOR CLEANING AND DRYING ANESTHESIA AND RESPIRATORY EQUIPMENT

[75] Inventors: Craig S. Sundheimer, Erie; Bradley D. Joslin, Cambridge Springs, both of Pa.

[73] Assignee: American Sterilizer Company, Erie, Pa.

[21] Appl. No.: 199,187

[22] Filed: Oct. 21, 1980

[51] Int. Cl.³ .......................... B08B 3/02; B08B 9/02
[52] U.S. Cl. .................................. 134/152; 134/102; 134/170
[58] Field of Search ............... 134/94, 99, 102, 166 R, 134/166 C, 170–171, 152

[56] References Cited

U.S. PATENT DOCUMENTS

| | | | |
|---|---|---|---|
| 2,526,265 | 10/1950 | Nulph | 134/171 X |
| 2,652,842 | 9/1953 | Hayes | 134/171 X |
| 3,062,227 | 11/1962 | Soderberg | 134/170 X |
| 3,070,104 | 12/1962 | Faust et al. | 134/152 X |
| 3,601,135 | 8/1971 | Marlow et al. | 134/166 R X |

FOREIGN PATENT DOCUMENTS 821464  7/1949  Fed. Rep. of Germany ... 134/166 R

*Primary Examiner*—Robert L. Bleutge
*Attorney, Agent, or Firm*—Robert D. Yeager

[57] ABSTRACT

An apparatus for cleaning and drying articles of anesthesia and respiratory equipment, particularly corrugated tubing and breathing bags. The corrugated tubes are threaded onto vertically arranged, perforated pipes which have restricted flow passages at their ends. First cleaning liquid, then drying air, is supplied under pressure to the pipes for radially outward flow therefrom to impinge on the lumina of the tubes.

7 Claims, 7 Drawing Figures

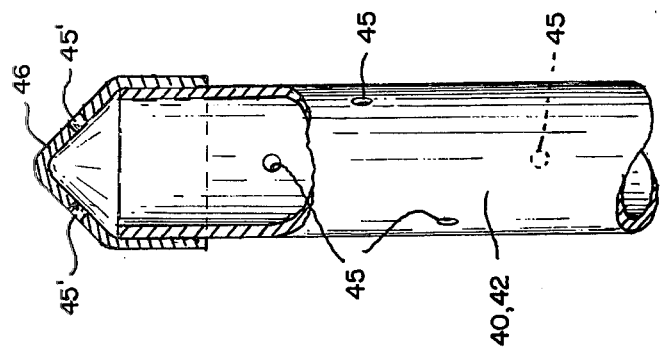
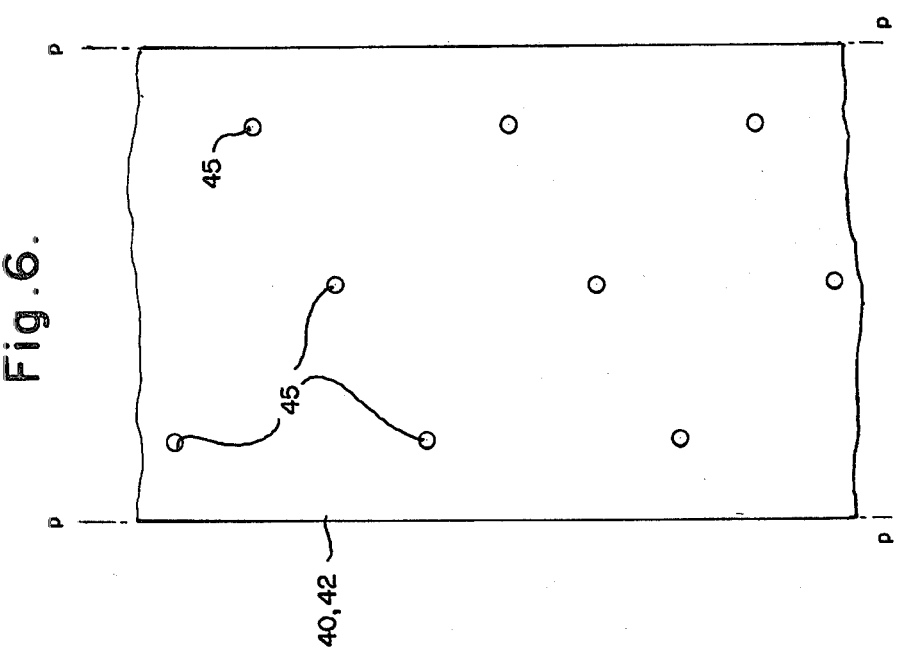
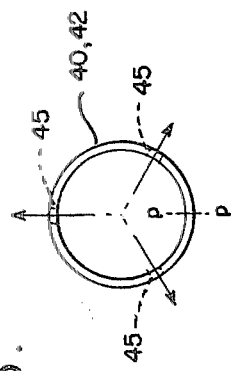
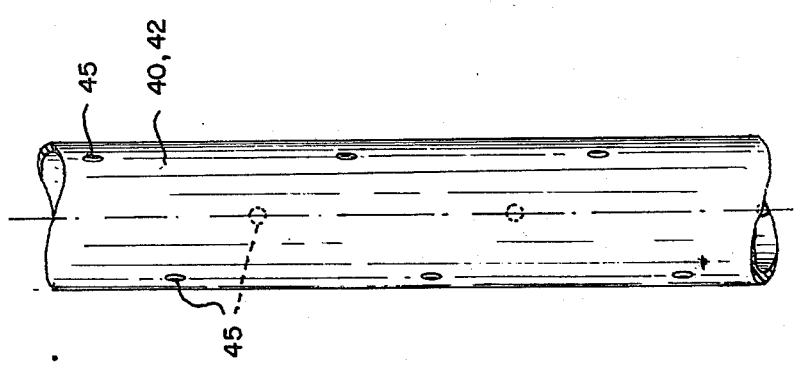

APPARATUS FOR CLEANING AND DRYING ANESTHESIA AND RESPIRATORY EQUIPMENT

BACKGROUND OF THE INVENTION

1. Field of the Invention

This invention relates to a apparatus for cleaning and drying anesthesia and respiratory equipment.

2. Description of the Prior Art

The need for thorough cleaning, disinfecting and drying of anesthesia and respiratory therapy (hereinafter "ART") equipment in hospitals is well recognized. The materials of construction and the structure of such equipment have posed serious obstacles, however, to achieving that objective. Flexible, corrugated tubing, which is widely used in forming breathing tubes, breathing bags and other accessory ART items generally are formed of synthetic materials that are subject to deterioration and even destruction when exposed to classical sterilization and disinfection procedures used, for example, with hospital hard goods. Accordingly, care must be exercised in the selection of temperatures and cleaning agents that may be used with ART items.

A further, and perhaps more formidable problem associated with the proper cleaning and disinfection of ART equipment is, however, their peculiar structures. The undulating surfaces of corrugated tubing pose a challenge to cleaning, particularly in the interior (lumen) of such tubing; and breathing bags and other cul-de-sac configurations present similar difficulties by reason of their structure.

The classic approach to cleaning such ART items has been to subject them to axial flow of cleaning/disinfecting agent and drying air; i.e. introducing the fluid into one end of the hollow article, permitting axial flow along its length, and permitting egress of the fluid at the distal end. The efficacy of this technique with tubular items will be discussed shortly; the complete inapplicability of the technique to cul-de-sac items having only a single opening is apparent.

It is well known that the characteristics of fluid flow within a tube involve a transverse profile having maximum flow rates in the center of the tube and diminishing flow rates radially outwardly, approaching zero at the tube wall. To be effective, cleaning and drying must occur at the tube wall; thus, axial flow offers limited efficiencies in the cleaning and drying of ART equipment. Representative of the use of axial flow techniques is British Pat. No. 1,168,035.

SUMMARY OF THE INVENTION

The present invention overcomes the problems associated with conventional techniques of cleaning and drying ART equipment by providing a flow of media (wash water, rinse water, disinfection fluid or drying air) directed substantially normal to the interior surfaces of the ART equipment items. In the particular case of corrugated tubing, for example, the media is carried in a tube inserted into the lumen of a length of corrugated tubing and flows radially outwardly from the inserted tube to impinge substantially perpendicularly upon the surfaces of the lumen. In this manner, cleaning and drying are optimized because the energy of the cleaning or drying media is concentrated at the surface of the lumen. Similar principles are applied by the present invention in the cleaning and drying of ART items having cul-de-sac configurations, such as breathing bags.

The present invention provides apparatus for cleaning and drying lengths of corrugated tubing, hollow articles and other items constituting components of anesthesia and respiratory equipment comprising: a main chamber; a plurality of substantially vertically arranged pipes disposed within the main chamber, each pipe being adapted to receive the lumen of a length of corrugated tubing; each pipe having one end in selective fluid communication with a source of cleaning liquid and a source of air; means for selectively supplying under pressure to the pipes cleaning liquid and air from their respective sources; and each pipe further having longitudinally and circumferentially spaced ports for permitting the liquid and alternately the air present under pressure in the pipe to flow radially outwardly therefrom and into contact with the surrounding lumen. Preferably, the ports in adjacent longitudinal rows along each pipe are transversely staggered.

In a preferred form, the present invention provides that the substantially vertical pipes include at least one pair of axially aligned pipes, one suspended from the top of the main chamber and the other supported by the floor of the main chamber, having their adjacent ends spaced apart from one another. In another preferred form, the present invention further comprises means disposed within the main chamber for spraying cleaning liquid onto the exterior surfaces of corrugated tubing surrounding the pipes; and means for directing air into contact with those exterior surfaces after the main chamber spray means is deactivated. The apparatus of the present invention also may include an auxiliary chamber; a plurality of upstanding pipes disposed within the auxiliary chamber, each such pipe being adapted to extend into the interior of a hollow flexible bag and support it; each such upstanding pipe having its lower end in selective fluid communication with the pressurized sources of cleaning liquid and air, respectively; and each such upstanding pipe further having longitudinally and circumferentially spaced ports for permitting liquid and alternately air, supplied under pressure to the upstanding pipe, to flow radially outwardly therefrom and into contact with the interior surfaces of the hollow bag. The auxiliary chamber preferably also is equipped with means for spraying cleaning liquid onto the exterior surfaces of the bag and with means for directing air into contact with those exterior surfaces after the auxiliary spray means is deactivated.

Other details and advantages of the present invention will become apparent as the following detailed description, taken with the accompanying drawings, proceeds.

BRIEF DESCRIPTION OF THE DRAWINGS

FIG. 4 is an enlarged side elevational view of a portion of the perforated pipe used in the present invention;

FIG. 5 is a diagrammatic end view of the pipe shown in FIG. 4, illustrating the manner of developing the pipe segment shown in FIG. 4;

FIG. 6 is a development of the pipe segment of FIG. 4, made by severing the pipe at the line p—p of FIG. 5; and FIG. 7 is a side elevational view, with portions broken away for clarity, of the free end of the perforated pipe used in the present invention, showing a perforated cap thereon.

DETAILED DESCRIPTION OF THE PREFERRED EMBODIMENTS

Figure 1:
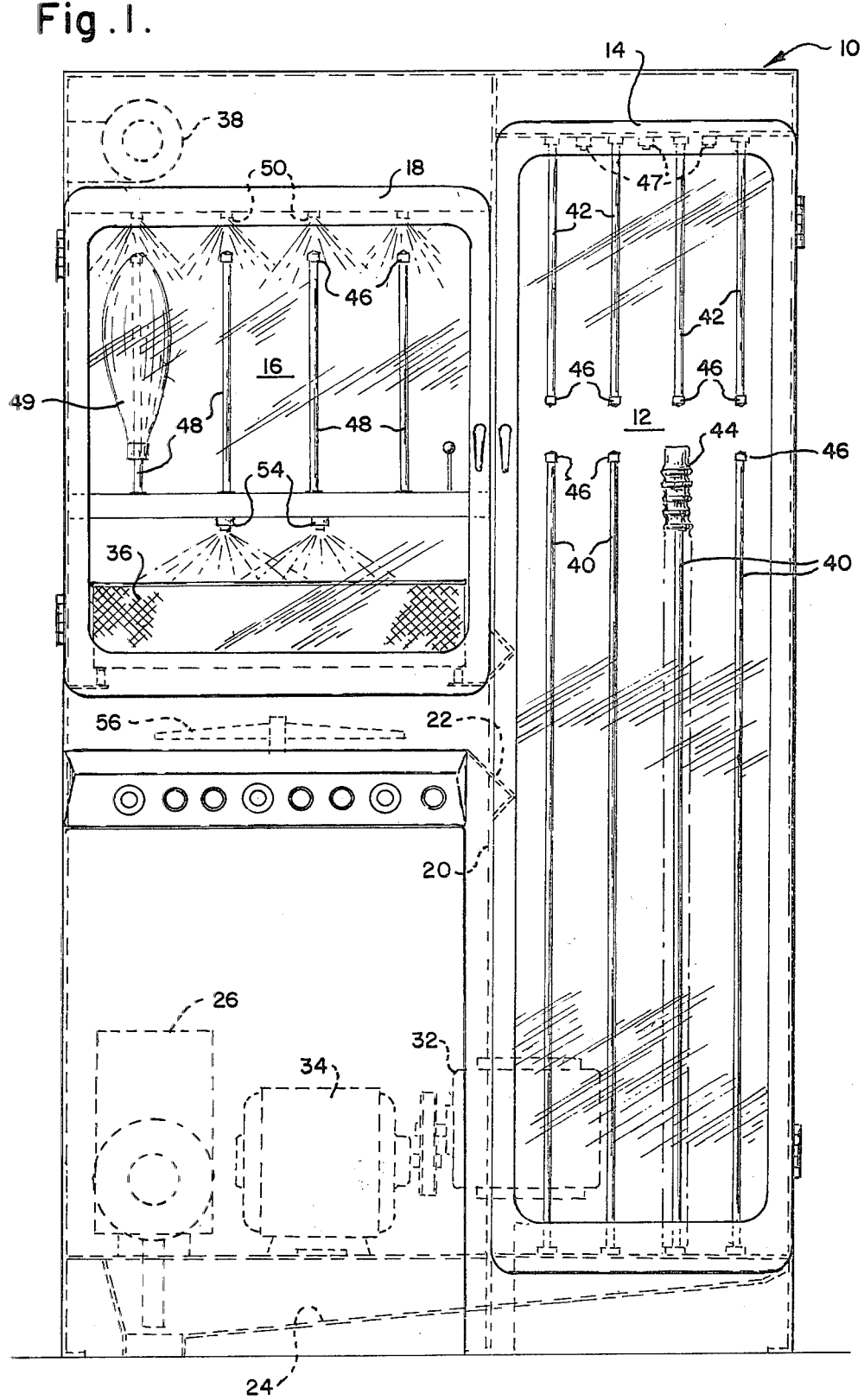
FIG. 1 is a front elevational view, with portions removed for clarity, of apparatus incorporating the present invention.
Figure 2:
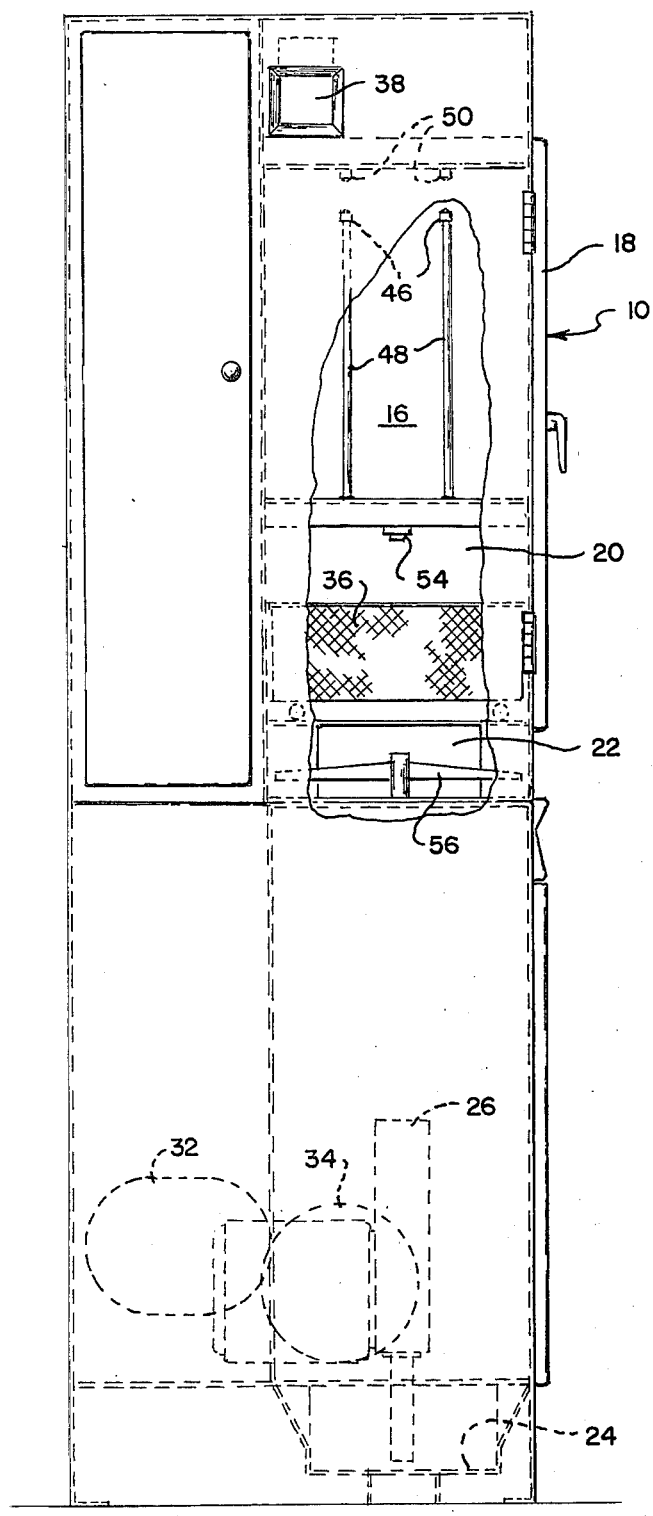
FIG. 2 is an end elevational view, with portions removed for clarity, of the apparatus shown in FIG. 1 as viewed from the left side of FIG. 1.
Figure 3:
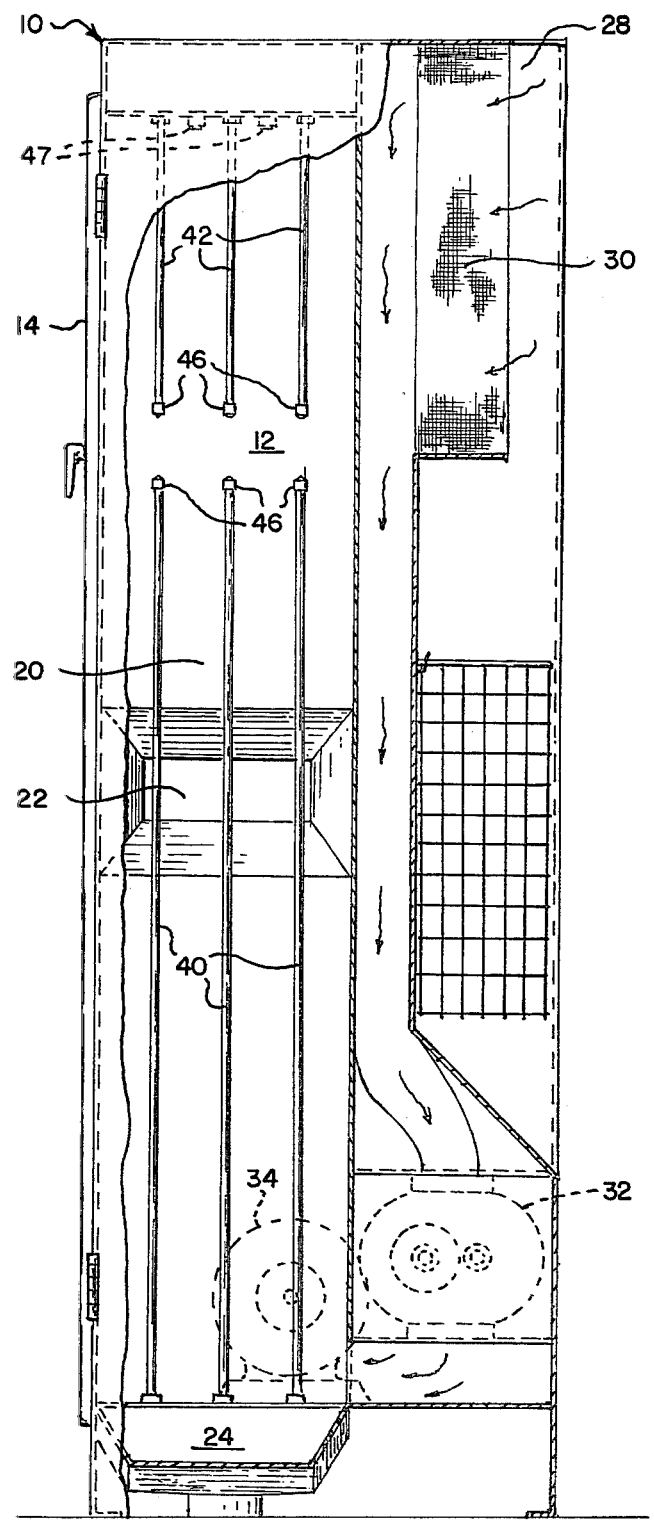
FIG. 3 is an end elevational view, with portions removed for clarity, of the apparatus shown in FIG. 1 as viewed from the right side of FIG. 1.

Referring to the drawings, particularly to FIGS. 1–3, there is shown a cabinet 10 embodying the apparatus of the present invention. Cabinet 10 includes a main chamber 12, accessible via side-hinged door 14, and an auxiliary chamber 16, accessible via oppositely-hinged door 18. Doors 14 and 18 are constructed to effectively seal chambers 12 and 16 against water leakage from washing or disinfecting processes occurring within those chambers. Chambers 12 and 16 are separated by septum 20 which has a rectangular port 22 to provide fluid communication between the chambers.

Cabinet 10 has a liquid holding tank 24 located in its base. Liquid collected in auxiliary chamber 16 can flow through port 22 in septum 20 and thence into main chamber 12. Liquid collected in main chamber 12 flows through a strainer (not shown) in the floor of main chamber 12 and is returned to holding tank 24. Liquid may be withdrawn from holding tank 24 by pump 26 for distribution under positive pressure through a system of piping and valves (not shown) to the active spray components of the present invention soon to be described.

Cabinet 10 also is equipped with an air distribution system. Outside air enters the system through port 28 (see FIG. 3) and passes through filter 30, which preferably removes both bacteria and dust from the air to provide sterile air. The sterile air then flows downwardly (as shown by the arrows in FIG. 3), past a noise reduction unit and through a heating duct (not shown), and enters the inlet side of blower 32, which is driven by motor 34. The hot, sterile air then is distributed through a system of air lines and valves to the active components of the present invention soon to be described. Air flow within cabinet 10 generally is from main chamber 12, through port 22 of septum 20, upwardly through accessory basket 36 (described below) and into auxiliary chamber 16, and further upwardly to be exhausted at the top of auxiliary chamber 16 by exhaust blower 38.

Referring now to FIGS. 1 and 3, the means for cleaning, disinfecting and drying lengths of corrugated tubing within main chamber 12 now will be described. Chamber 12 is shown having four rows of substantially vertically arranged upstanding pipes 40, with three pipes in each row. Axially aligned with each upstanding pipe 40 is a suspended pipe 42.

Each pipe 40 is adapted to receive the lumen of a length of flexible corrugated tubing 44 of the type used in ART equipment and as illustrated diagramatically in FIG. 1. Tubing 44 is threaded onto pipes 40; if the length of a particular segment of tubing exceeds the length of pipe 40, the top end of the tubing is threaded over the free end of the corresponding suspended pipe 42 and the tubing is pushed upwardly onto suspended pipe 42 to prevent the occurrence of any kinks or bends in the tubing.

As best shown in FIGS. 4–7, pipes 40 and 42 are perforated with circumferentially and longitudinally spaced fluid flow passages 45. The passages are intended to provide radially outward flow of any fluid present under pressure in pipe 40, 42. It is apparent that when a length of corrugated tubing is threaded onto pipe 40, 42, this fluid will impinge upon the lumen of the tubing at substantially right angles.

Pipes 40, 42 may be formed of any suitable material such as aluminum or brass. In typical length, pipes 40 are 45 inches to accommodate ART tubes that most often are 42 inches in length. The outside diameter of pipes 40, 42 must be less than the smallest ART tubing inside diameter but large enough to pass sufficient drying air at relatively low pressure. A typical outside diameter is 0.5 inches or less. Generally, perforations 45 are no smaller than 1/32 inch because of practical drilling considerations, a typical diameter being 0.031 inches.

As shown in FIG. 6, perforations 45 preferably are arranged in three longitudinal rows, each row being 120° apart from the others. Further, the perforations in adjacent rows are longitudinally staggered. Typically, a perforation 45 in one of the longitudinal rows occurs every 9/32 inches of pipe length.

As shown in FIG. 7, the free ends of pipes 40, 42 are constructed to have a restricted flow passage to permit maintenance of positive fluid pressures within the pipes. In the embodiment of the present invention shown in the drawings, this restricted flow passage takes the form of a perforated cap 46 soldered onto the end of pipe 40, 42. Cap 46 has a conical end section with three perforations 45' (only two shown in FIG. 7) located in the sloping portions of that section, 120° from one another. Perforated cap could be replaced by a solid cap or a crimped end section.

Pipes 40, 42 are mounted to the bottom and top, respectively, of main chamber 12. The inlet ends of pipes 40, 42 are suitably connected by manifolds (not shown) to the liquid and air distribution systems discussed above in such a way that first liquid may be introduced under pressure into pipes 40, 42; then, when the liquid distribution system is deactivated, heated, sterile air from the air distribution system may be introduced under pressure into pipes 40, 42. Spray heads 47 mounted at the top of main chamber 12 and also suitably connected to the liquid distribution system provide means for applying liquid spray to the exterior surfaces of corrugated tubing threaded on pipes 40, 42 in the main chamber.

Turning now to auxiliary chamber 16, the means for cleaning, disinfecting and drying breathing bags and accessory ART equipment will now be described. Chamber 16 is shown as having four rows of vertically arranged upstanding pipes 48, with two pipes in each row. Pipes 48 are constructed and mounted identically to pipes 40 (within main chamber 12) except that pipes 48 are of shorter length (typically 17 inches) to accommodate standard size ART breathing bags 49 as shown on the left-hand pipe 48 of auxiliary chamber 16. Further, pipes 48 preferably vary in material of construction from pipes 40 in that, while pipes 40 are preferably rigid, pipes 48 may be constructed of flexible material, or of a rigid material with a hinged base, to permit them to be bent in order to facilitate loading and unloading of breathing bags. Pipes 48 are suitably connected to a manifold which, in turn, may be selectively connected with the liquid and air distribution systems in the same manner as discussed above in respect of pipes 40, 42. Wide angle spray heads 50 mounted at the top of auxiliary chamber 16 and also suitably connected to the liquid distribution system provide means for applying liquid spray to the exterior surfaces of breathing bags mounted on pipes 48.

Also located within auxiliary chamber 16 is a removable accessory basket 36 into which may be placed a variety of ART accessory items such as breathing masks and the like. Spray heads 54, mounted above accessory basket 36 and connected to the liquid distribution system, provides means for applying liquid spray to ART items contained in accessory basket 36. Disposed beneath accessory basket 36 is rotatable spray arm 56 which also is connected to the liquid distribution system. Spray arm 56 serves to apply liquid spray to the underside of items contained within accessory basket 36.

A typical wash/disinfection and drying procedure employing the apparatus of the present invention will now be described. Lengths of corrugated tubing are loaded into main chamber 12, breathing bags are loaded into auxiliary chamber 16, and accessory items of ART equipment are loaded into accessory basket 36, all as described above. The wash cycle is commenced by withdrawing water, present from the previous rinse cycle, from holding tank 24 and charging the water to the liquid distribution system. Water enters pipes 40 and 42 and is sprayed from perforations 45, 45' of those pipes to wash the lumina of corrugated tubing 44 mounted on the pipes. Likewise water enters perforated pipes 48 in auxiliary chamber 16 and washes the interiors of breathing bags 49 mounted on pipes 48. Water also is sprayed from spray heads 54 and rotating spray arm 56 to wash the top sides and bottom sides, respectively, of sundry accessory items in accessory basket 36. Further, water is sprayed from wide angle spray heads 50 to wash the exterior surfaces of breathing bags 49 in auxiliary chamber 16. Finally, water is sprayed from spray heads 47 located in main chamber 12 to wash the exterior surfaces of corrugated tubes 44 in that chamber. Water is collected in auxiliary chamber 16 and passes to main chamber 12 through port 22 in septum 20. Before passing into holding tank 24, water collected at the base of main chamber 12 passes through a strainer (not shown) in the floor of main chamber 12 that removes macroscopic debris. Water returning to holding tank 24 is withdrawn and the cycle is repeated.

A rinse cycle may be accomplished in the same manner as the wash cycle. If a disinfection is necessary, the water in holding tank may be heated to about 170° F. by heaters (not shown) located in holding tank 24; this technique accomplishes disinfection through pasteurization. Also, chemical disinfection may be accomplished by adding suitable disinfectants to the water. A combination of pasteurization and chemical disinfection may also be used. When the liquid cycles have been completed, the liquid distribution system in cabinet 10 is deactivated and the unit is switched to the drying mode.

One of the advantages of the present invention over conventional washing and drying techniques for ART equipment is that the ART components need not be handled between the wash/disinfection and drying processes. Hot, sterile air is charged to the air distribution system as described above and is forced under pressure to pipes 40, 42 and 48. The air emerges from perforations 45, 45' of those pipes and impinges on the interior surfaces of the corrugated tubing and breathing bags in the same manner as liquid impingement occurs. In the particular case of corrugated tubing, the air impinges substantially at right angles to the lumina of the tubing and is highly effective in drying the undulating surfaces of the lumina. The air emerges from the tubing 44 and the breathing bags 49 and flows to exhaust blower 38 in the manner described above. This air flow serves to dry the exterior surfaces of the corrugated tubing, the breathing bags and the accessory items in accessory basket 36.

In a typical unit embodying the present invention, air flow rates may be relatively low, e.g. less than 20 CFM per pipe. When the air flow rate is optimized, it should be observed that, in general, the total area of the perforations 45, 45' in a single pipe 40, 42, 48 should not exceed the cross-sectional area of the pipe. By observing this relationship, a margin of safety is provided because the inlet flow to a single pipe should be less constrained than the perforation outlet flows in order to maintain uniform static pressure within the pipe. Any static pressure gradient along the length of a perforated pipe will result in an uneven flow pattern.

The drying efficiency of the present invention may be enhanced by manipulation of the corrugated tubes in main chamber 12, as by vertical oscillation and/or rotation. Other variations that may be employed to improve drying efficiencies include capping one end of the corrugated tube and optionally, venting the cap to provide a flutter action, and pulsing the air supply. During efficiency also may be improved by heating the drying air to further elevated temperatures compatible with the materials of construction involved.

The use in the present invention of radial flow patterns as contrasted with axial flow used in conventional apparatus has improved vastly the efficiency of cleaning ART equipment and markedly shortened the time required to dry the equipment after cleaning. As a consequence, overall hospital safety benefits. While what has been described above is a batch-type process, the speed and efficiency achieved by the method and apparatus of the present invention clearly may lend the invention to continuous operation.

What is claimed is:

1. Apparatus for cleaning and drying lengths of corrugated tubing, hollow articles and other items constituting components of anesthesia and respiratory equipment comprising:
    a main chamber;
    a plurality of substantially vertically arranged pipes disposed within said main chamber, each said pipe being adapted to receive the lumen of a length of said corrugated tubing;
    each said pipe having one end in selective fluid communication with a source of cleaning liquid and a source of air;
    means for selectively supplying under pressure to said pipes cleaning liquid and air from said respective sources; and
    each said pipe further having longitudinally and circumferentially spaced ports for permitting said liquid and alternately said air present in said pipe under pressure to flow radially outwardly therefrom and into contact with said surrounding lumen.

2. Apparatus as recited in claim 1 wherein:
    said ports in adjacent longitudinal rows along said pipe are transversely staggered.

3. Apparatus as recited in claim 1 wherein said plurality of vertically arranged pipes includes:
    at least one pair of axially aligned pipes, one suspended from the top of said main chamber and the other supported by the floor of said main chamber, having their adjacent ends spaced apart from one another.

4. Apparatus as recited in claim 1, which apparatus further comprises:
means disposed within said main chamber for spraying cleaning liquid onto the exterior surfaces of corrugated tubing surrounding said pipes; and
means for directing air into contact with said exterior surfaces after said main chamber spray means is deactivated.

5. Apparatus as recited in claim 1, which apparatus further comprises:
an auxiliary chamber;
a plurality of upstanding pipes disposed within said auxiliary chamber, each said upstanding pipe being adapted to extend into the interior of a hollow flexible article and support it;
each said upstanding pipe having its lower end in selective fluid communication with said pressurized sources of cleaning liquid and air, respectively; and
each said upstanding pipe further having longitudinally and circumferentially spaced ports for permitting said liquid and alternately said air, supplied under pressure to said upstanding pipe, to flow radially outwardly therefrom and into contact with the interior surfaces of said hollow article.

6. Apparatus as recited in claim 5, which apparatus further comprises:
means disposed within said auxiliary chamber for spraying cleaning liquid onto the exterior surfaces of said hollow article disposed therein; and
means for directing air into contact with said exterior surfaces of said hollow article after said auxiliary spray means is deactivated.

7. Apparatus as recited in claim 5, which apparatus further comprises:
means within said auxiliary chamber for supporting sundry components of anesthesia and respiratory equipment for exposure to said auxiliary spray means and said air.

* * * * *

UNITED STATES PATENT AND TRADEMARK OFFICE
CERTIFICATE OF CORRECTION

PATENT NO. : 4,354,514

DATED : October 19, 1982

INVENTOR(S) : CRAIG S. SUNDHEIMER et al.

It is certified that error appears in the above-identified patent and that said Letters Patent are hereby corrected as shown below:

Column 6, Line 25, delete "During" and substitute therefor --Drying--.

Signed and Sealed this

Fifteenth Day of February 1983

[SEAL]

Attest:

GERALD J. MOSSINGHOFF

Attesting Officer

Commissioner of Patents and Trademarks